United States Patent
Tregub et al.

(10) Patent No.: US 7,048,434 B2
(45) Date of Patent: May 23, 2006

(54) THERMAL ANALYSIS AND CHARACTERIZATION OF LAYERS AND MULTIPLE LAYER STRUCTURES

(75) Inventors: Alex Tregub, Oak Park, CA (US); Mansour Moinpour, San Jose, CA (US); David Fryer, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 388 days.

(21) Appl. No.: 10/247,048

(22) Filed: Sep. 17, 2002

(65) Prior Publication Data

US 2004/0054495 A1 Mar. 18, 2004

(51) Int. Cl.
*G01N 25/20* (2006.01)
(52) U.S. Cl. .............................. 374/10; 374/31; 374/36; 374/43; 374/45
(58) Field of Classification Search .................. 374/10, 374/31, 36, 43, 45
See application file for complete search history.

(56) References Cited

U.S. PATENT DOCUMENTS

| | | | |
|---|---|---|---|
| 5,217,305 A | * | 6/1993 | Yamakawa et al. ........... 374/45 |
| 5,342,892 A | * | 8/1994 | Vanderbilt et al. .......... 525/168 |
| 5,869,647 A | * | 2/1999 | Narayan et al. ............ 536/107 |
| 6,054,868 A | | 4/2000 | Borden et al. |

FOREIGN PATENT DOCUMENTS

JP  08284646 A  * 10/1996

* cited by examiner

*Primary Examiner*—Stephen Stein
(74) *Attorney, Agent, or Firm*—Blakely, Sokoloff, Taylor & Zafman LLP

(57) ABSTRACT

Thermally analysis of layers and multiple layer structures used in the semiconductor processing arts is disclosed. A modulated calorimetric analysis may be used to determine a thermal signature that characterizes the chemical properties of a sample of material. The signature may include one or more thermal properties such as heat capacities. The signature may be used to compare and infer the suitability of a material for use in an integrated circuit manufacturing process. A thermal signature for a material that is not known to be suitable for manufacturing integrated circuits may be compared with a thermal signature for a standard material that is known to be suitable in order to determine whether the aforementioned material is suitable. Multiple layer structures may also be analyzed, compared, and inferred, and approaches for determining thermal signatures for any individual layer of the multiple layer structure are disclosed.

19 Claims, 6 Drawing Sheets

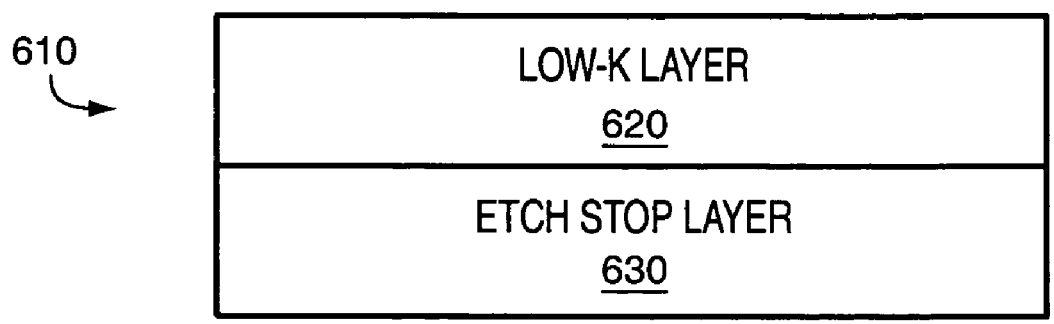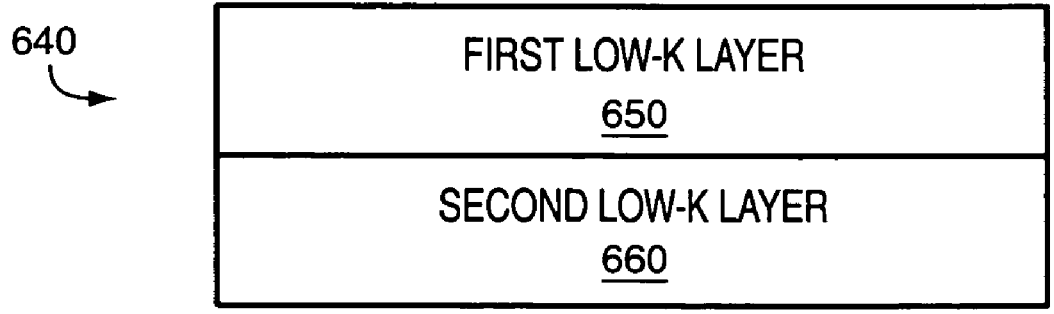
FIG. 6

THERMAL ANALYSIS AND CHARACTERIZATION OF LAYERS AND MULTIPLE LAYER STRUCTURES

BACKGROUND

1. Field

Embodiments of the present invention relate to the thermal analysis of layers and multiple layer structures used in the semiconductor processing arts.

2. Background Information

A variety of layers and multiple layer structures are in widespread use in the semiconductor processing arts. Exemplary layers include among others resists, anti-reflective coatings, and low dielectric constant layers. These layers and their properties have an important impact upon the overall semiconductor manufacturing process, on the yield of integrated circuits, and on the quality and reliability of the integrated circuits produced. Unfortunately, one of the significant problems with the use of such layers it variability in the properties of the materials used to form the layers. The existing methods for analyzing and characterizing these types of layers and their properties are limited, especially in the case of the characterization and analysis of multiple layer structures.

BRIEF DESCRIPTION OF THE SEVERAL VIEWS OF THE DRAWINGS

The invention may best be understood by referring to the following description and accompanying drawings that are used to illustrate embodiments of the invention. In the drawings:

FIG. 6 shows exemplary multiple layer structures that may be analyzed, according to embodiments of the invention.

DETAILED DESCRIPTION

Figure 1:
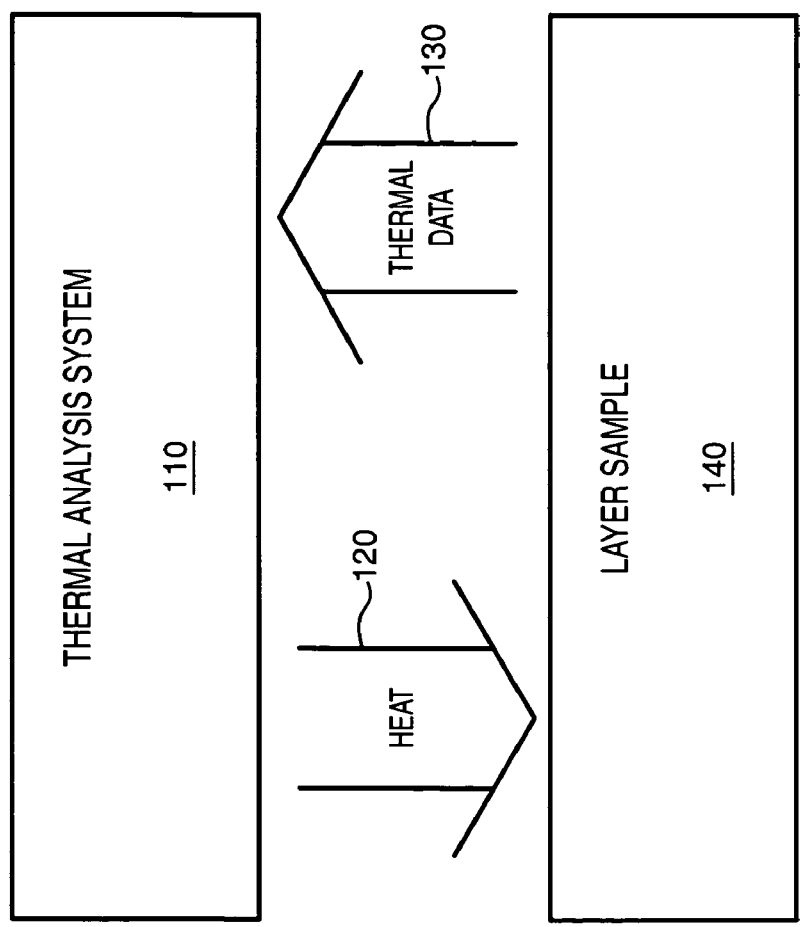
FIG. 1 shows a thermal analysis system for analyzing a layer and collecting data sufficient to characterize the layer with a thermal signature containing one or more thermal properties, according to embodiments of the invention.

Described herein are systems and methods for thermal analysis and characterization of single layers and multiple layer structures. In the following description, numerous specific details are set forth. However, it is understood that embodiments of the invention may be practiced without these specific details. In other instances, well-known circuits, structures and techniques have not been shown in detail in order not to obscure the understanding of this description.

I. Thermal Analysis of Single Layers

Embodiments of the present invention allow for the thermal analysis of a single layer such as a resist, a radiation sensitive layer, a low dielectric constant layer, a polymeric layer, or other layers. In general, a sample of the layer is placed in a suitable thermal analysis system and analysis is performed to characterize the layer and to determine a thermal signature containing one or more thermal properties that contain information about the chemical structure of the layer. The thermal signature identifies a layer and allows it to be compared to other layers. The concepts are further illustrated in the following sections through the thermal analysis of a radiation sensitive resist layer, although the invention is not limited to the analysis of resists, and the systems and methods disclosed herein are also applicable to the analysis of other layers and multiple layer structures.

A. Analysis of Resists

Resists and other radiation sensitive layers are used extensively in the semiconductor manufacturing industry in order to manufacture integrated circuits. The resists are commonly exposed to patterned radiation from a lithography system. The lithography system often includes a radiation source that generates and transmits a dose of radiation towards a resist layer formed over a semiconductor substrate. The radiation is commonly an electromagnetic radiation such as light, ultraviolet light, x-rays, etc. or a particle beam such as an electron beam, which has been patterned with circuitry information relevant to the manufacture of the integrated circuit by passing radiation from the source through a patterned mask. The patterned radiation impacts and exposes the resist. During exposure a material in the resist is transformed, often through the building or breaking of chemical bonds. The transformations make the exposed portions of the resist selectively difficult or easy to remove by a developer. Two common types of radiation sensitive layers are positive resists in which the radiation causes the exposed portions to become more soluble in a developer and negative resist in which the radiation causes the exposed portions to become less soluble in a developer. The particular types of chemical and structural transformations depend upon the particular resist and may include such processes as crosslinking, cleavage, chemical amplification, catalysis, and the like. Based on these patterned exposures and transformations, integrated circuits may be created or formed on the substrate through conventional processes, such as development, etching, doping, and the like, which are regarded to be well known in the semiconductor processing arts.

The inventors have discovered that thermal analysis may be used to characterize radiation sensitive layers, such as resists, and provide a window into the chemical, physical, and structural properties of exposed and unexposed radiation sensitive layers. In a sense, the thermal characterization may be used as a thermal sensitometry for characterizing and understanding the chemical and structural response of the resist to radiation exposure and development. FIG. 1 shows a thermal analysis system 110 that may be used to calorimetrically analyze a layer by adding heat 120 to a sample from a layer 140 and measuring corresponding thermal response data 130 that characterizes the layer, according to embodiments of the invention. The system often adds heat to the layer, measures resulting temperature increases in the layer, and determines a variety of thermal properties, such as heat capacity, thermal conductivity, or glass transition temperature, which characterize the layer and incorporate information about the chemistry and structure of the layer. In the case of resists these properties are often dependent upon the amount of radiation exposure and provide information about the amount of radiation induced transformations in the layer.

A number of thermal analysis systems are suitable. In one instance, which will be discussed further below, the system is a modulated differential scanning calorimetry (MDSC) system. Experiments by the present inventors indicated that the MDSC systems are useful for performing the methods described herein. The inventors additionally contemplate that other systems may also be useful, such as other differential scanning calorimetry (DSC) systems, differential thermal analysis (DTA) systems, sample controlled thermal analysis (SCTA) systems, and the like.

The inventors have discovered that certain thermal properties, such as the heat capacity among others, capture and provide information about the chemical and structural properties of the resist. The heat capacity is a well-known thermal property for a material that relates the amount of heat exchanged with the material to the corresponding change in temperature of the material. In particular, the heat capacity quantifies the amount of heat needed to raise the temperature of a given quantity of material by one degree in temperature. The heat capacity may be readily determined by DSC systems, MDSC systems, and other thermal analysis systems. In the case of the MDSC system, the system determines the heat capacity automatically and internally based on the heat provided to the sample and the thermal data collected from the sample using a single MDSC run. The heat capacity in effect divides in the appropriate units the amount of heat added to a sample by the mass of the sample and the change in temperature within the sample as a result of the added heat. Determining a heat capacity with a MDSC system is well known in the arts.

In the case of many commercially available polymeric resists, as well as other polymeric materials generally, the heat capacity may capture information about, and characterize, the degree of crosslinking and internal molecular motion within the resist. Crosslinking tends to tighten and constrain internal molecular motion within the resist making it harder and less flexible and able to move. Generally, lesser degrees of crosslinking within the resist, and correspondingly greater degrees of freedom for internal molecular motion, lead to correspondingly higher heat capacities due to more venues of vibration and molecular motions that may absorb and store heat. For example, a resist with many short and highly mobile polymeric chains may have a comparatively high heat capacity due to storage of heat within internal motion and vibration within the many flexible polymeric chains, while a resist with high crosslinking and few mobile polymeric chains may have a comparatively low heat capacity due to the lack of places to store heat in the form of internal molecular motion. The inventors have also found that other thermal properties such as the glass transition temperature also characterize the structure of a resist and may also be used as a thermal signature, according to embodiments of the invention. Of course the structure and degree of crosslinking also have implications on development and subsequent processing of the resist. Therefore an ability to characterize the chemical structure and degree of crosslinking with a thermal signature that includes a heat capacity, glass transition temperature, or other thermal incantation of the structure, would be useful for determining the suitability of the resists for a particular integrated circuit manufacturing process.

To further illustrate the concepts, consider the following exemplary thermal analysis that characterizes a resist with a thermal signature that represents the chemistry and structure of the resist. The particular analysis is performed on a KRF® Series M73Y photoresist, which is available from JSR Corporation of Tokyo, Japan. This photoresist is a positive acting resist that is based on chemical amplification. Alternatively, other resists could also be used. Initially, the resist was formed on semiconductor substrates by using conventional spinning methods. Some of the resist on the substrates were exposed to various ultraviolet radiation doses in the range of approximately 0–1 $mJ/cm^2$. Samples of both the exposed and unexposed resist were taken by scraping the resist from the substrates with a blade. The weight of the sample was measured and recorded in the analysis software (within the MDSC system) for calculations.

Figure 2:
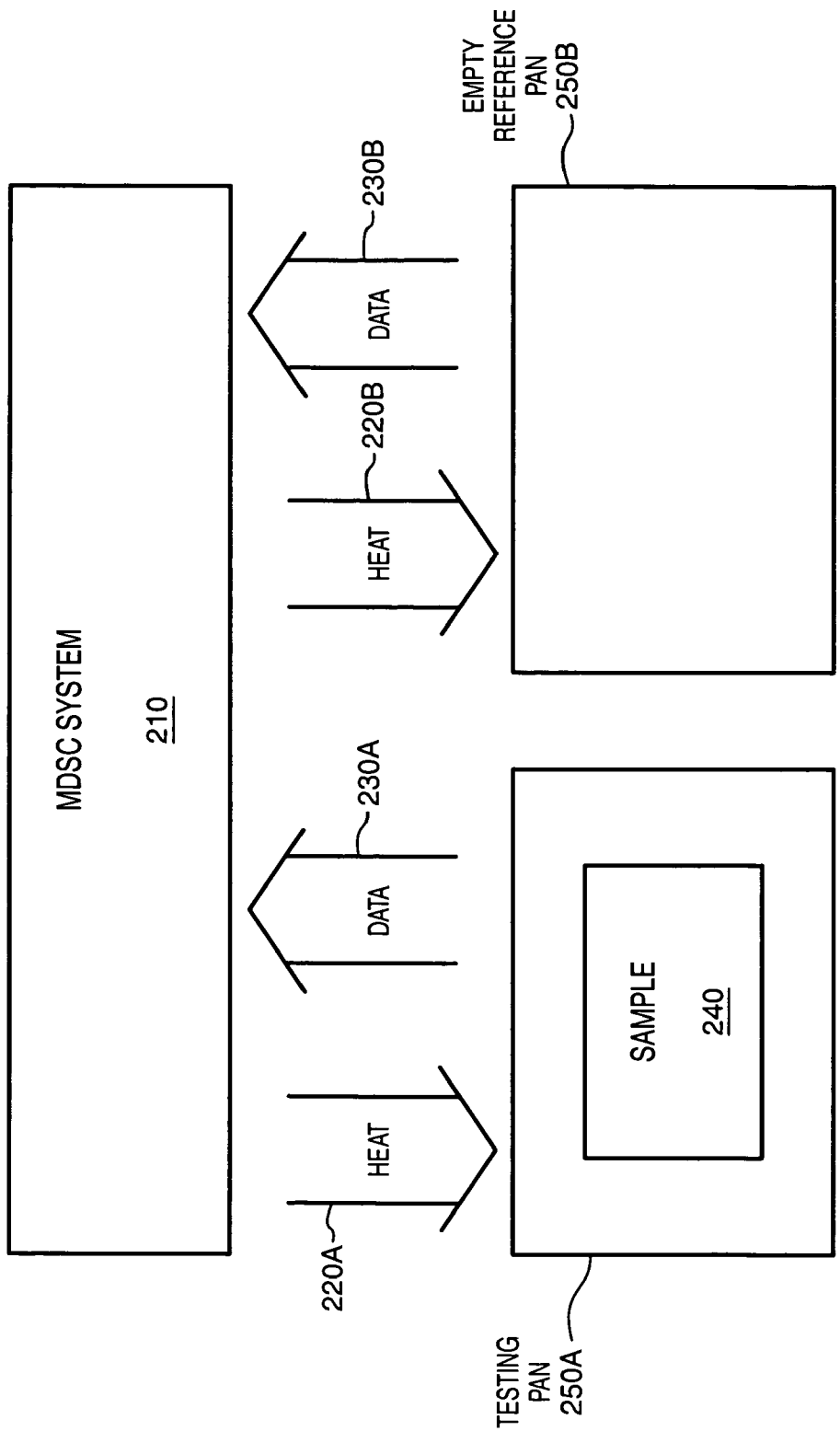
FIG. 2 shows a thermal analysis system for analyzing a multiple layer structure and collecting data sufficient to characterize an individual layer of the structure, according to embodiments of the invention.

The samples of the exposed and unexposed resist were analyzed with the MDSC system shown in FIG. 2. In this particular example, the inventors used a Model 2690 Modulated Differential Scanning Calorimetry (MDSC) System, available from TA Instruments of New Castle, Del. Of course other MDSC systems are available from other vendors, such as PerkinElmer, Inc. of Wellesley, Mass. MDSC systems have been used extensively for purposes of thermal analysis materials. Of course, other calorimetry and thermal analysis systems may also be used.

Background information on MDSC systems and their use is available from a number of sources. A general discussion of the use of MDSC systems in thermal analysis is provided in, "Modulated Differential Scanning Calorimetry—A New Way Forward in Materials Characterization", by M. Reading, published in Trend. Polym. Sci., 8: 248 (1993). More discussion on MDSC is available from B. Wunderlich et. al., Thermochimica Acta, 348: 181 (2000), Van Mele et. al., Polymer, 42: 1449 (2001), and numerous other sources. Useful background information on the operation and use of MDSC systems is also commonly available from MDSC system vendors, such as TA Instruments, PerkinElmer, etc. Of course, other calorimetry and thermal analysis systems may also be used.

The MDSC system 210 was used to determine heat capacities of the sample at different temperatures. For thermal analysis, a sample 240 was sealed in a testing container or pan 250A, and was added to the thermal analysis chamber of the MDSC system along with a reference empty container or pan 250B. The tests were conducted in the inert atmosphere, in this case nitrogen, to exclude oxidation in the air. The MDSC system exchanged heat 220A with the testing pan and heat 220B with the reference pan in the analysis chamber and collected corresponding calorimetric data 230A–B from the testing pan and reference pan, respectively. In this particular example, temperatures were measured with thermocouples, one for each of the two pans, although in other embodiments employing different analysis systems, the calorimetric data may include electrical power balance data, or direct measurements of heat absorbed or released from the sample. The calorimetric data may be used to calculate heat released or absorbed by the sample during the MDSC run. In any event, the calorimetric data may be used to calculate a heat capacity or other desired thermal property of the sample. The reference container or pan may allow the effect of the testing container or pan to be removed or eliminated from the determination of the heat capacity of the sample in order to provide a more accurate and representative value for the sample. The MDSC system contains an internal electrical differentiator to remove the calorimetric data or signals 250B associated with the reference pan from those associated with the testing pan 250A. Of course removing the effect of the pan is not required.

The MDSC system employed a modulated thermal analysis to make dynamic, non-steady-state calorimetric measurements on the sample under analysis by using modulated heating rates. In one example, the sample may be heated according to a linear temperature ramp that is modulated with a superimposed wave. One suitable superimposed wave is a sinusoidal wave having a regular period and typically small amplitude relative to the linear temperature ramp. Of course, other waves such as other curvilinear waves, square waves, zig-zag waves, or other fluctuations or modulations that may be superimposed to perform a modulated thermal analysis may also be used. Such a modulated thermal analysis often provides a richer quality of information about the sample compared to a non-modulated thermal analysis. Depending upon the particular implementation, the temperature of the MDSC scans may be varied over the range of approximately −150–400° C. In these particular experiments the temperature was ramped between an initial temperature of approximately −40° C. (which was a convenient lower bound for the particular MDSC system) to a final temperature in the range of approximately 200–250° C. with a temperature ramp rate of approximately 3° C./minute. The final temperature was selected since it was high enough to drive some of the uncompleted radiation induced transformations but was not so high that the resist would thermally degrade. Of course, different starting temperatures, ending temperatures, and temperature ramp rates may be used, as desired. As another alternative, the analysis could also be performed with a cooling ramp. The inventors have found that it is often desirable to induce transformation of the resist in order to determine such information as the degree of completion of the transformation or crosslinking reactions in the resist. The oscillating or modulated temperature was superimposed on the underlying temperature ramp in order to separate heat related to reversing (e.g., vitrification) and non-reversing (e.g., cure) chemical processes and to obtain heat capacity values in a single MDSC run. This may provide a characterization of both the reversible and non-reversible thermal behavior of a sample, which is often beneficial for materials such as polymeric resists that exhibit both behaviors. In the particular calorimetric analysis, the modulation wave was a sinusoidal wave with an amplitude of approximately ±1° C. and a period in the range of approximately 60–80 seconds in order to allow for several modulations, in this case about four, to be included in the thermal analysis.

Figure 3:
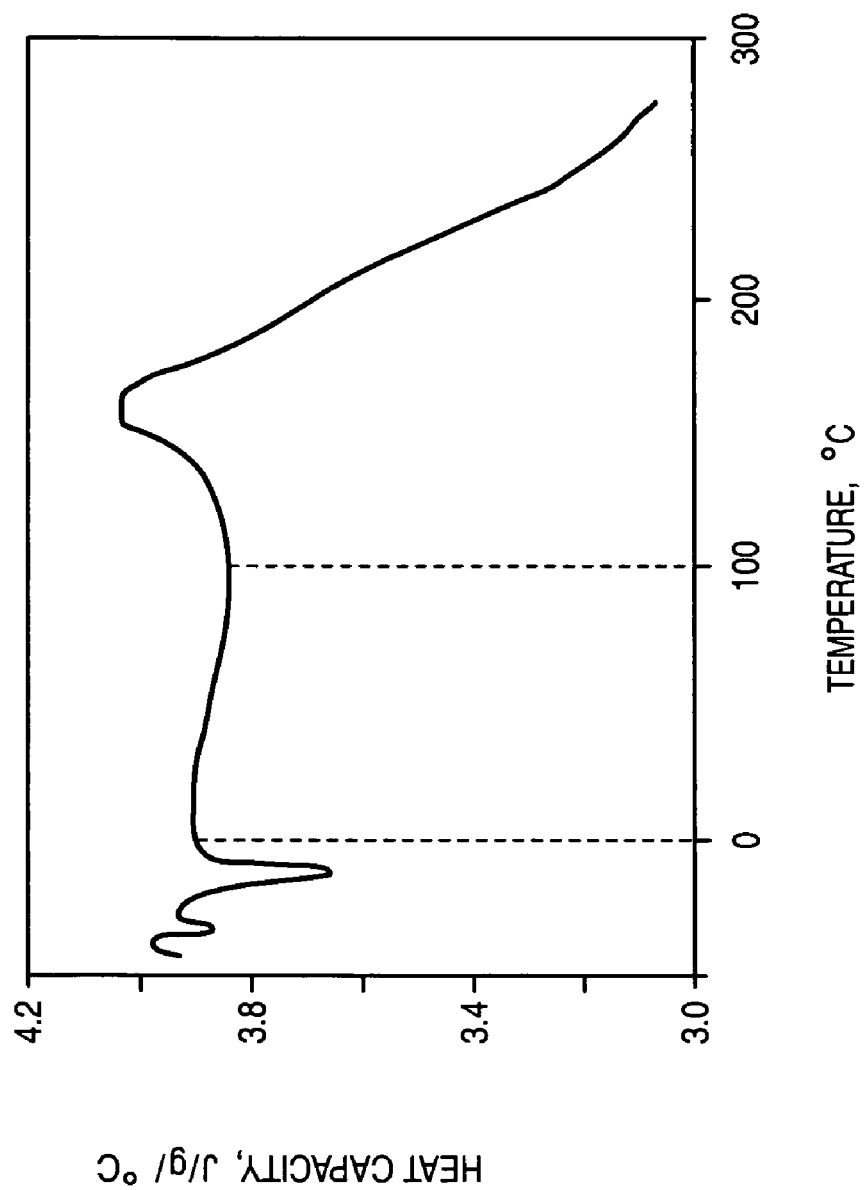
FIG. 3 shows heat capacities determined for a resist layer as a function of temperature by a modulated differential scanning calorimetry (MDSC) system, according to embodiments of the invention.

FIG. 3 shows heat capacities determined as a function of temperature for a sample of unexposed resist, according to embodiments of the invention. As shown, the heat capacities were determined in the range of approximately −40–250° C. The heat capacity has a strong and irregular temperature dependency below approximately 0° C. This may be due to freezing or like physical transformations occurring within the resist. The heat capacity has a comparatively weak and regular dependency with temperature in the range of approximately 0–100° C., or slightly higher. Each of the heat capacities measured in this range are comparatively similar in magnitude. The heat capacity has a local maximum in the range of approximately 150–160° C. Starting at approximately 150–160° C. and up to approximately 250° C. the heat capacity has a strong and nearly constant inverse (decreasing) dependency with temperature. This may be due to partly reversible and partly irreversible temperature-induced transformation of the resist. In this range, the temperature may encourage or promote some of the same crosslinking transformations caused by the radiation exposure.

The thermal data shown in FIG. 3 provides a thermal signature, according to one embodiment of the invention that provides a substantial amount of information about the structure and chemistry of the resist. Alternatively, the large amount of thermal information shown in FIG. 3 is often not needed in order to sufficiently characterize a resist. Any single heat capacity, at any one of the temperatures, may serve as a thermal signature, according to alternate embodiments of the invention. For example, a heat capacity measured at a temperature in the range of approximately 0–100° C. may serve as a thermal signature of a resist. The heat capacity measured in this range of temperatures may have the advantage of being nearly stable and should facilitate reliable measurement. Alternatively, the local maximum in the heat capacity may be incorporated into a thermal signature and used to characterize the resist. In other resists, local minimum, abrupt changes in the heat capacity, and other inflections may be useful for characterizing the resist. Even the single heat capacities may characterize and identify the chemical structure of the resist, for example quantifying how much, if any, crosslinking exists in the resist. Alternatively, two or more heat capacities may serve as a thermal signature of a resist. Heat capacities may be measured at various temperatures in a single MDSC run, or in two subsequent MDSC runs for the same sample, known as "first heat" and "second heat" runs. For example, a first heat capacity measured at a temperature in the range of approximately 0–100° C. and a second heat capacity measured at a maximum in the range of approximately 100–200° C. may serve as a thermal signature of a resist. The incorporation of the heat capacity measured at the higher temperature in the thermal signature may help characterize and identify the degree of completion of the crosslinking transformations in the resist, since the higher temperatures may encourage or drive these transformations.

The inventors also contemplate repeating the thermal analysis of a sample, by applying a second MDSC run (second heat) after an initial first MDSC run (the first heat) has been completed. For example, after the analysis of the sample that is represented in FIG. 3, the sample may be subjected to a similar subsequent thermal analysis. Although not required, the repeat thermal analysis may provide additional information and characterization of the degree of completion of the crosslinking transformations in the resist. If such a repeat thermal analysis of the same sample is desired, the thermal signature may include a first heat capacity from the first thermal analysis and a second heat capacity from the second thermal analysis. For example, a first heat capacity measured at a temperature in the range of approximately 0–100° C. in the first thermal analysis and a second heat capacity measured at a temperature in the range of approximately 0–100° C. in the second thermal analysis may serve as a thermal signature characterization of a resist.

Analogous thermal signatures may be obtained for exposed resists. The signatures for the exposed resists may provide direct and relevant characterization of the transformation of the resist due to the radiation and the chemistry, structure, and amount of crosslinking in the resist that make it suitable or unsuitable as it goes forward into development and subsequent integrated circuit manufacturing processes. As one example, the resist may contain a different amount of initiator or catalyst. This would often not be detected by the thermal analysis of the unexposed resist, since the initiators or catalysts would likely be in low concentration and have a very small affect on thermal properties, but would often be detected by the thermal analysis of the exposed resist, since the different amount of initiator or catalyst would likely affect the crosslinking and thereby affect the thermal properties.

B. Using Thermal Signatures to Compare and Make Inferences About Resists

A significant problem with the use of resist layers in the manufacture of integrated circuits is variability in the chemical properties of the resists that can lead to reduction in process yields or degraded integrated circuit performance and reliability. One situation that is commonly encountered in a integrated circuit manufacturing process is the receipt of a new resist, which may be reported to have particular properties, but for which the actual properties are unknown, unconfirmed, untested, or unvalidated. For example, the new resist may be from a new batch of resist available from the same vendor, which may have different chemical properties as compared to the resists from the previous batches, or the new resist may be from a different vendor and may have different properties. The cause of the variation may include such factors as different chemical compositions, different manufacturing conditions, different starting materials, different age of the resist, different exposures to extremes of temperature, and other such factors.

Regardless of the reason for the variability, if the chemical properties of the resist are different than expected, the resist may have a different and unexpected sensitivity and response to an exposure to radiation, which is generally undesirable since it may lead to inconsistent transformations and ultimately may lead to numerous problems such as decreased process yields and degraded integrated circuit performance and reliability. For example, for many resists it is well known that the degree of crosslinking of exposed resists is an important property that affects the suitability of the resist for development and subsequent processes in a particular integrated circuit manufacturing process. If the crosslinking is either too high or too low the resist may not be satisfactory. The manufacturing process may be developed or optimized for a resist having particular characteristics and may be poorly suited for handling resists with different characteristics. A new resist, a resist from a new batch, or a resist with otherwise unknown, unconfirmed, untested, or unvalidated properties may be thermally analyzed to determine a thermal signature and that thermal signature compared with a thermal signature of a standard resist sample in order to make inferences about the suitability of the resist.

Figure 4:
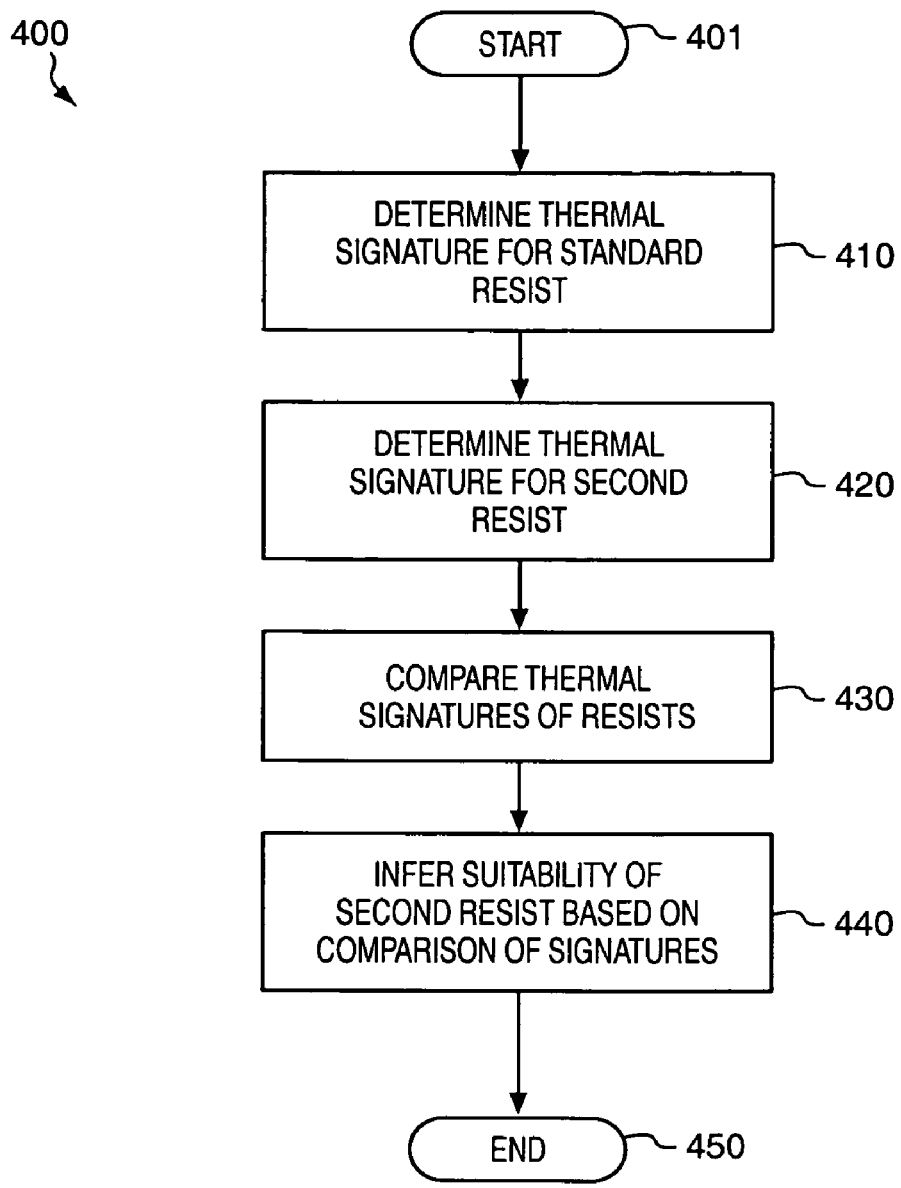
FIG. 4 shows a method for inferring the suitability of a resist based on a comparison of a thermal signature for the resist with a thermal signature for a standard resist, according to embodiments of the invention.

FIG. 4 shows a method 400 for inferring the suitability of a resist based on a comparison of a thermal signature for the resist with a thermal signature for a standard resist, according to embodiments of the invention. The method allows inferring whether a particular resist material, which may be from a new vendor or batch, is suitable for a particular integrated circuit manufacturing process for which a predetermined standard resist is known to be sufficient for manufacturing integrated circuits. The method may be used, during development, during pilot scale testing, or as part of a quality control program, to infer whether a resist is suitable before extensive and widespread use of the resist in mass volume production of integrated circuits. The application of the method may provide more confidence that the resist will behave satisfactorily, and as expected, in the current integrated circuit manufacturing process, and may reduce the risk of using a resist that would perform unsatisfactorily and unexpectedly and thereby cause a significant reduction in process yields, expense, and integrated circuit performance and reliability. This may avoid a costly discovery, after widespread use of the resist, that the resist had an unexpected chemistry, structure, or other property that was not well suited to a particular integrated circuit manufacturing process.

The method initiates at block 401 and then advances to block 410 where a thermal signature is determined for a standard resist. As used herein, the term standard sample, standard resist, and the like, will be used to refer to a sample that has been set up or otherwise established as a reference to which other samples may be measured or compared. The standard sample may be a sample of a material that is known to be satisfactory, suitable, acceptable, and valid for its intended use in manufacturing good integrated circuits, for example in a particular integrated circuit manufacturing process. This knowledge may be due to extensive testing or experimentation, based on a prior history of satisfactory performance in manufactured integrated circuits, because the resist was used to develop the process, or based on other knowledge that the standard resist is suitable. The particular process used to manufacture the integrated circuits may be based on the standard resist and may be relatively intolerant or not well suited to deviations in characteristics from the standard resist. The standard resist may but need not have improved characteristics compared to other resists inasmuch as it may merely be adopted for the manufacturing process by convention. The standard resist may set the standard or specification for resists. Another resist that is sufficiently close in the necessary characteristics to the standard resist may be said to meet specification, or be "in spec", whereas a resist that is different in these characteristics from the standard resist may be said to be out of specification, or "out of spec".

The standard resist is thermally analyzed with an MDSC or other suitable thermal analysis system in order to obtain a thermal signature for the resist. As discussed above, the thermal signature captures chemical and structural information about the resist and serves as an identification or fingerprint for the resist. This thermal signature may be preserved and used as a standard or reference for comparison to thermal signature characterizations of other resists that are not known to be sufficient. Table 1 provides one exemplary thermal signature that the inventors contemplate to be useful for comparison of resists. This signature may be obtained by a thermal analysis such as described above.

TABLE 1

THERMAL SIGNATURE OF STANDARD RESIST

| RADIATION EXPOSURE | THERMAL ANALYSIS | HEAT CAPACITY AT 50° C. (J/g/° C.) | MAXIMUM HEAT CAPACITY (J/g/° C.) |
| --- | --- | --- | --- |
| UNEXPOSED | FIRST HEAT | 3.88 | 4.06 |
| UNEXPOSED | SECOND HEAT | 3.49 | 3.69 |
| EXPOSED | FIRST HEAT | 3.46 | 3.52 |
| EXPOSED | SECOND HEAT | 3.09 | 3.09 |

The third and fourth columns of the Table 1 list heat capacity data determined for samples of the resist. The first column identifies whether the heat capacities in the third and fourth columns are for an unexposed sample or for a sample that has been exposed to a dose of radiation. The second column identifies whether the heat capacities are for a first thermal analysis (first heat) of a sample or a second thermal analysis (second heat) of a sample. The third column lists the heat capacities determined for the samples at a temperature of 50° C. As shown in FIG. 3, the heat capacity for this particular resist is relatively stable at this temperature. As an alternative, other temperatures in the range of approximately 0–100° C. may be used. The fourth column lists the maximum heat capacity determined for the sample. For this particular resist, the maximum heat capacity typically occurred in the range of approximately 150–160° C.

The heat capacities of the unexposed resist tend to be higher than the heat capacities of the exposed resist. This may be due to crosslinking reactions that tend to tighten and decrease the internal molecular mobility of the resist and thereby reduce stores for thermal energy that increase the heat capacity. It is also noteworthy that, even though the radiation dose was fairly small (e.g., not greater than approximately 1 mJ/cm$^2$), the heat capacities measured for the unexposed resist are significantly different than those measured for the exposed resist. This indicates that the heat capacity provides a highly sensitive measurement of even small chemical and structural changes in the resist. Such small changes are often difficult to detect or undetectable by prior art techniques, such as those based on contact angle measurement.

The heat capacities determined for the repeat thermal run (second heat) of the same sample are lower than heat capacities of the initial run (first heat). This may be due to temperature induced transformations that analogously to the exposure induced transformations tend to tighten the structure of the resist and allow its polymeric constituent chains to have less movement and freedom of movement which may translate into reduced degrees of translation, rotation, vibration, and less ability to store heat and increase the heat capacity.

The present inventors have found that the heat capacities listed in Table 1 provide a convenient thermal signature and characterization for a resist material. Of course, in alternate embodiments of the invention, rather than so much characterizing data, a thermal signature may include a single heat capacity, for example a maximum heat capacity, or a heat capacity in the temperature range of testing (e.g., in the range of approximately 50–100° C.).

The method advances from block 410 to block 420 where a thermal signature of a second resist is determined. The second resist may be a resist from a different vendor, a resist produced by a different process, a resist produced in a different batch, or may be otherwise not established with the desired level of confidence to be suitable for manufacturing integrated circuits in the particular process. The thermal signature for the second resist may be determined as previously described. Typically, the thermal signature for the second resist will be determined with the same equipment and procedures as the thermal signature for the standard resist in order to avoid potential differences due to the thermal analysis rather than to actual differences in the resists.

The method advances from block 420 to block 430 where the thermal signatures of the standard resist and second resist are compared in order to determine whether the signatures are sufficiently similar. The comparison may be a formalized rigorous analytical or statistical comparison or an informal comparison, as desired. The thermal analysis system may be programmed to perform such comparisons automatically to a stored signature for the standard resist.

The comparison may include determining the difference between the signatures. A comparison may be made between one or more heat capacities of the thermal signatures for the standard and the second resists. For example, an absolute value of a difference between a maximum heat capacity for a standard resist and a maximum heat capacity for the second resist may be determined or calculated. As another example, the difference, or absolute value of the difference, of a plurality of heat capacities, or other thermal properties, determined for the second resist and the standard resist may be determined as an indication of the difference between the characteristics of the standard and second resists. Of course, numerous other ways of comparing the thermal signatures are contemplated, as will be appreciated by a person having an ordinary level of skill in the art and the benefit of the present disclosure. For example, ratios may be used rather than differences.

The method advances from block 430 to block 440 where an inference is made regarding the suitability or unsuitability of the second resist based on the comparison of the thermal signatures. In particular, the second resist is inferred to be suitable if the thermal signatures are sufficiently similar and the second resist is inferred to be unsuitable if the thermal signatures are not sufficiently similar. The inference may include comparing a difference, ratio, equation, or other comparison of block 430 to a threshold. In various other implementations, depending upon the tolerance of the implementation for variation in resist properties, the second resist may be determined to be suitable if the maximum heat capacities are not different by more than approximately 1%, 5%, 10%, or 20%, or some other predetermined threshold. The determination of whether the difference is small or large should take into consideration such factors as the uncertainty of the heat capacity of the standard resist due to acceptable variation and due to uncertainty of measurement. It also should take into consideration how much the difference between heat capacities of different resist affects the output parameters of the integrated circuit manufacturing process. The standard deviation of several such measured heat capacities may provide one such indication of the uncertainty. As stated above, the sufficiency may depend upon the tolerance of the manufacturing process for variations in the chemical structure and other characteristics of the resist. In one particular instance, the second resist may be inferred unsuitable if the heat capacity of the second resist differs from the heat capacity of the standard resist by more than one standard deviation of the heat capacity of the standard resist. In another instance where the process is more tolerant to variation, two or more standard deviations may be used. Of course the use of standard deviations are not required and the comparison could be made to a fixed percentage (e.g., 10%) of the heat capacity of the standard resist. Other measures of sufficiency, including statistical measures, are contemplated. If possible, the similarity may be assessed relative to both a resist that is known to be sufficient and a resist that is known to be insufficient based on actual use in manufacturing integrated circuits. The determination of whether the difference is small or large may also take into consideration how big the difference would be for a resist know not to work. For example, if there is a small difference between a standard resist and a known unsuitable resist or the same resist type, even a small difference in the heat capacities for the standard and second resist may be significant. For example, the heat capacity of the second resist may be compared to a first heat capacity of a standard resist and a second heat capacity of a resist that is known to be insufficient. Then, the second resist may be inferred to be suitable or satisfactory if its heat capacity is closer to the heat capacity of the standard resist or inferred to be unsuitable and unsatisfactory if its heat capacity is closer to the heat capacity of the resist that is known to be insufficient.

The method may be repeated for additional unconfirmed resists, as desired, or may terminate at block 450.

Those skilled in the semiconductor processing arts and having the benefit of the present disclosure will appreciate that the method is not limited to comparison of resists and may be used to compare and infer the suitability of other types of materials used in the semiconductor processing arts.

II. Thermal Analysis of Multiple Layer Structures

The inventors have discovered approaches for thermally analyzing multiple layer structures containing two or more united layers and elucidating or estimating thermal characteristics, properties, and contributions of a single separate individual layer of the structure. This may allow thermally characterizing the single separate individual layer with a thermal signature, which may be used as described elsewhere herein, for example to allow comparison with a standard.

To illustrate the concepts consider the following non-limiting example in which a multiple layer structure comprising a resist on an anti-reflective layer and an individual resist are separately analyzed to determine a thermal signature for the anti-reflective layer. Initially, a first sample of the multiple layer structure is analyzed to determine a thermal property (e.g., a heat capacity) for the structure. Separately, a second sample of an individual resist layer is analyzed to determine a thermal property (e.g., a heat capacity) for the resist layer. Then, the thermal property of the anti-reflective layer, which was not directly measured, may be estimated or inferred from the thermal properties determined for the structure and the individual resist layer.

The particular multiple layer structure of this example contained a KRF® Series M73Y resist deposited on a SLAM anti-reflective layer (available from TOKYO OHKA KOGYO CO., LTD. of Kawasaki, Kanagawa, Japan). Initially, the anti-reflective layer was formed on an integrated circuit substrate, for example a semiconductor wafer, by using conventional methods that are well known in the semiconductor processing arts. The KRF® Series M73Y resist was then formed on the anti-reflective layer, by conventional spinning methods, to form a multiple layer structure on the substrate. The multiple layer structure and the resist were exposed to a dose of approximately 1 mJ/cm$^2$ of extreme ultraviolet radiation. Of course this is not required and in other analysis unexposed resists may be analyzed. The M73Y resist was formed on another substrate and exposed to a dose of approximately 1 mJ/cm$^2$ of extreme ultraviolet radiation. The individual resist and the resist in the structure are of the same type and were formed consistently so that they should have similar thermal properties. There may be some small differences, for example due to one resist being formed on the anti-reflective layer while the other is formed on the substrate directly, although these are expected to be small.

Samples of the multiple layer structure and the individual resist were removed from the substrates with a blade. The samples were loaded into a MDSC system, such as that shown in FIG. 2, and analyzed. The particular thermal analysis system was a Model 2690 MDSC system as previously described, although this is not required. Initially, a sample of the multiple layer structure was analyzed in a first heat. The sample was sealed in the testing pan and loaded into the thermal testing chamber along with the empty reference pan. In this particular analysis, the MDSC system was operated in a modulated mode involving ramping the temperature from approximately −40° C. to approximately 250° C. at a rate of about 3° C./minute and modulating the temperature ramp with a superimposed sinusoidal wave having an amplitude of about 1° C. and a period of about 60–80 seconds, although this is not required. Heat capacities at 50° C. and maximum heat capacities in the range of approximately 150–160° C. were determined. Next, the sample was reanalyzed in a second heat. Heat capacities at 50° C. and maximum heat capacities in the range of approximately 150–160° C. were determined. Next, a sample of the individual resist layer was analyzed in a first heat. The sample was sealed in the testing pan and loaded into the thermal testing chamber along with the empty reference pan. Heat capacities at 50° C. and maximum heat capacities in the range of approximately 150–160° C. were determined. Next, the sample was reanalyzed in a second heat. Heat capacities at 50° C. and maximum heat capacities in the range of approximately 150–160° C. were determined. Table 2 lists the 50° C. and maximum heat capacities determined for the structure and the resist in the first heat and second heat.

TABLE 2

THERMAL ANALYSIS OF MULTIPLE LAYER STRUCTURE

| RADIATION EXPOSURE | THERMAL ANALYSIS | HEAT CAPACITY AT 50° C. (J/g/° C.) | MAXIMUM HEAT CAPACITY (J/g/° C.) |
|---|---|---|---|
| RESIST | FIRST HEAT | 3.47 | 3.52 |
| RESIST | SECOND HEAT | 3.09 | 3.09 |
| RESIST + ARC | FIRST HEAT | 2.59 | 2.87 |
| RESIST + ARC | SECOND HEAT | 2.32 | 2.53 |

Any comparison of the heat capacities of the structure and the individual resist layer may be a thermal signature for the anti-reflective layer, according to embodiments of the invention. A difference between one or more heat capacities of the structure and the resist may be a thermal signature for the anti-reflective layer. For example, a difference between the maximum heat capacities determined for the individual resist and the structure in the first heat, calculated as 0.65=(3.52−2.87), may be an exemplary thermal signature or property for the anti-reflective layer. A ratio of one or more heat capacities of the structure and the resist may be a thermal signature for the anti-reflective layer. For example, a ratio of 50° C. heat capacities determined for the resist and the structure during the second heat, calculated as 0.77=(3.09/2.32), may be an exemplary thermal signature or property for the anti-reflective layer. Other comparisons are contemplated.

The thermal property or thermal signature estimated or inferred for the anti-reflective layer may be used to characterize its chemical structure, its mechanical properties, its ability to adhere to a substrate, thermal stability, etc. In some embodiments, the thermal signature determined for the sample of the anti-reflective layer may be compared to a thermal signature for a standard anti-reflective layer sample known to be satisfactory for manufacturing integrated circuits in a particular process in order to infer whether or not the anti-reflective layer material would be satisfactory and be "in spec".

Thermal properties are often not available for individual layers of a multiple layer structure particularly for sublayers. Separating or isolating these sublayers from the overlying united layers is often difficult and the separation may in fact alter the characteristics of these layers. The approach described above allows thermally characterizing a layer, such as a sublayer, without separating or isolating the layer. Additionally, in some cases the sublayer may be modified or altered during the formation of the overlying layers, for example due to exposure to radiation or due to thermal pathways associated with the formation of the overlying layers. The approach described above allows thermally characterizing the layer subjected to such potential modifications with the further advantage of not needing to separate or isolate the layer.

Figure 5:
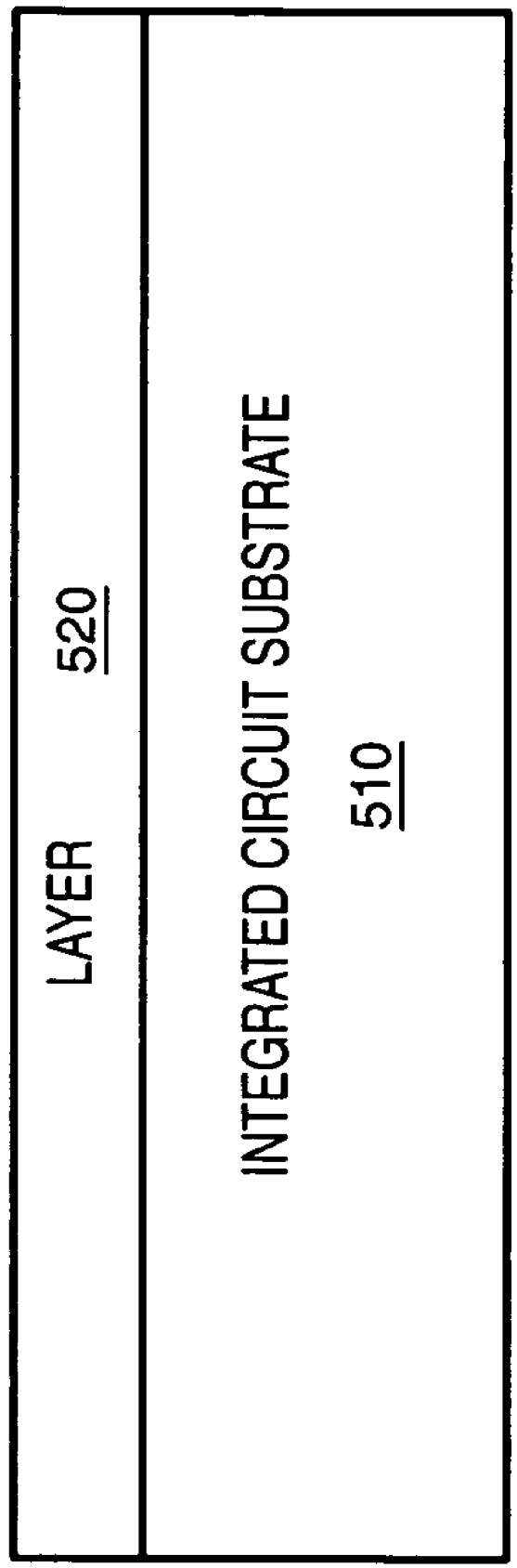
FIG. 5 shows an integrated circuit substrate having a layer formed thereon that has been inferred to be suitable by the method of FIG. 4, according to embodiments of the invention.

Embodiments of the invention allow manufacturing integrated circuits based on layers of materials that are inferred suitable by methods as disclosed herein. FIG. 5 shows an integrated circuit substrate having a layer that has been inferred to be suitable for manufacturing integrated circuits formed thereon, according to embodiments of the invention. The integrated circuit substrate may include a semiconductor substrate, a silicon wafer, or the like. The layer may be a resist, a low dielectric constant layer, an anti-reflective coating, an etch-stop layer, a polishing protective cap layer, or another known layer in integrated circuit manufacturing. In a first embodiment of the invention, the integrated circuit substrate may be a completed integrated circuit, such as a microprocessor, retaining at least a portion of the layer. For example, the integrated circuit may contain a low dielectric constant material or anti-reflective coating material that has been inferred to be suitable based on thermal analysis, comparison, and inference, as described herein. According to a second embodiment of the invention, the integrated circuit may be an intermediate substrate in an integrated circuit manufacturing process and the layer may be a resist layer that may be exposed by a lithography process, etched, chemically-mechanically polished, and otherwise processed by conventional techniques commonly used in the semiconductor processing arts in order to form transistors and circuits. Accordingly, an integrated circuit may be created or based on a material that has been inferred to be suitable by thermal analysis, comparison, and inference, as described herein.

Of course, the invention is not limited to the analysis of resists on anti-reflective layers and may be used to analyze other multiple layer structures. Any multiple layer structure may potentially be analyzed. FIG. 6 shows several non-limiting examples of other multiple layer structures that are suitable for thermal analysis by the systems and methods disclosed herein, according to embodiments of the invention. A first multiple layer structure 610 contains a low dielectric constant (low-k) layer 650 formed on an etch stop layer 660. The low-k layer has a dielectric constant less than that of silicon dioxide, which is about 3.9. Exemplary low-k dielectric layers are polymeric layers, such as organic SiLK layers available from The Dow Chemical Company of Midland, Mich., and the like. The etch stop layer may comprise silicon nitride, silicon carbide, or the like. A second multiple layer structure 640 contains a first low-k layer 650 formed on a second potentially different low-k layer 660. For such a multiple layer structure, a thermal analysis may be employed to characterize the adhesion and mechanical properties of the low-k material, for example to determine whether they are sufficient to avoid detaching from a substrate during polishing, or withstand chemical mechanical polishing without being mechanically damaged during polishing. Of course, numerous other multiple layer structures are contemplated. For example, another multiple layer structure includes a hardening cap layer with improved mechanical properties on top of a low-k layer to allow polishing.

Additionally, embodiments of the invention have been illustrated through the analysis of two-layer structures, in order to avoid obscuring the concepts of the present invention. However, other embodiments of the invention may be used to analyze structures containing three or more layers. As an example, a heat capacity of any single layer of a three-layer structure may be determined by analyzing a sample of the three-layer structure in one MDSC testing pan with the reference pan empty, and separately analyzing samples of each of the remaining two single layers (those excepting the single layer of interest) in the MDSC testing pan with the reference pan empty. That is, a multiple layer structure comprising the layers ABC may be analyzed, then the layer A alone may be analyzed, and then the layer C alone may be analyzed. Next, the thermal signature or property from each analysis may be compared in order to determine the signature or property for the remaining layer of interest. Of course, there are many other variations. As yet another example, the structure ABC and the structure AB may be separately analyzed and compared to determine the thermal signature for the layer C.

III. Modifying Exposure Dose Based on Thermal Properties

In integrated circuit manufacturing processes, resists and other radiation sensitive layers are exposed by using a lithography system including a radiation source that generates and transmits a dose of radiation towards the resist or radiation sensitive layer. The radiation sensitive layer is exposed and transformed by the radiation. For example, in the case of a positive resist, the radiation may chemically alter the resist so that exposed portions are more soluble in a given developer solution. As has been previously discussed, the resists may change. Also, the dose provided by the lithography system may change due to improper calibration, human error, or unexplained drift. Such variation is typically not desirable and may lead to varying extents of radiation sensitive layer transformation that may adversely affect both production yields and the quality and reliability of the manufactured integrated circuits.

The present inventors have discovered systems and methods for adjusting a radiation dose provided by a lithography system based on heat capacities or other thermal properties determined as described elsewhere herein. As an example, doses may be increased or decreased by respectively increasing or decreasing the time of exposure provided by a lithography system until the resists obtain a desired predetermined heat capacity. This may be used during development of a lithography process in order to obtain a particular dose that is desirable for a resist and with quality control to maintain a desired resist transformation while unexposed resist properties and transformation properties may potentially change.

The method may include exposing a radiation sensitive layer, such as a resist, to a particular dose of radiation from a radiation source. Then, the exposed layer may be thermally analyzed in order to determine a thermal signature containing one or more exposure dose dependent thermal properties for the layer. Next, the thermal signature or property may be used to determine whether the radiation dose used to expose the radiation sensitive layer is adequate. As one example, in a resist in which the heat capacity decreases due to exposure, if the determined heat capacity is found to be more than a predetermined desired heat capacity value (which may represent the desired extent of transformation of the resist) then the exposure time provided by the lithography system may be increased so that subsequently exposed resists are transformed to a greater extent and achieve heat capacities more proximate the predetermined value. As another example, in a resist in which the heat capacity increases due to exposure, if the determined heat capacity is found to be more than a predetermined heat capacity then the exposure time provided by the system may be decreased so that the desired extent of transformation of resists is achieved. Accordingly, a lithography system may be adjusted based on heat capacities or other thermal properties determined for exposed radiation sensitive layers. In this way, the total dose of radiation responsible for transforming the radiation sensitive layer may be changed in order to customize the transformation of the resist or make it match a predetermined extent of transformation.

A radiation sensitive layer that has been exposed to a dose of radiation from a radiation source that has been adjusted based a method that includes measuring a thermal property of a previously exposed radiation sensitive layer and adjusting the lithography system based on the thermal property is a product according to embodiments of the invention. Similarly, integrated circuits created by using these radiation sensitive layers are also products according to embodiments of the invention.

Embodiments of the present invention may include various operations, as described above. The operations may be performed by hardware components or may be embodied in machine-executable instructions, which may be used to cause a general-purpose or special-purpose processor or logic circuits programmed with the instructions to perform the operations. Embodiments of the invention may be provided as a computer program product that may include a machine-readable medium having stored thereon instructions that may be used to program a computer (or other electronic devices) to perform a process according to the present invention. The machine-readable medium may include, but is not limited to, floppy diskettes, optical disks, CD-ROMs, and magneto-optical disks, ROMs, RAMs, EPROMs, EEPROMs, magnet or optical cards, flash memory, or other type of media or machine-readable medium suitable for storing electronic instructions. Moreover, the instructions may also be downloaded as a computer program product, wherein the program may be transferred from a remote computer to a requesting computer by way of data signals embodied in a carrier wave or other propagation medium via a communication link (e.g., a modem or network connection). Alternatively, the operations may be performed by a combination of hardware and software.

Thus, systems and methods for thermal analysis and characterization of single layers and multiple layer structures have been described. While the invention has been described in terms of several embodiments, those skilled in the art will recognize that the invention is not limited to the embodiments described, but can be practiced with modification and alteration within the spirit and scope of the appended claims. The description is thus to be regarded as illustrative instead of limiting.

What is claimed is:

1. A method comprising:
   determining a thermal signature for a sample by calorimetrically analyzing the sample; wherein determining comprises determining a thermal signature for the sample of a resist; and
   comparing the thermal signature determined for the sample with a second thermal signature, wherein comparing comprises comparing the thermal signature determined for the sample of the resist with the second thermal signature determined for a sample of a second resist.

2. The method of claim 1, wherein the second resist comprises a material that is known to be suitable for manufacturing integrated circuits.

3. The method of claim 1, further comprising inferring whether a material corresponding to the sample is suitable for manufacturing integrated circuits based on the comparison of the thermal signatures.

4. The method of claim 1
   wherein determining the thermal signature comprises determining a heat capacity; and
   wherein comparing comprises comparing the heat capacity with a second heat capacity of the second thermal signature.

5. The method of claim 1
   wherein determining the thermal signature comprises determining a plurality of heat capacities at different temperatures; and
   wherein comparing comprises comparing the plurality of heat capacities with a second plurality of heat capacities of the second thermal signature determined at the different temperatures.

6. The method of claim 1, wherein determining comprises analyzing the sample with a modulated differential scanning calorimetric analysis.

7. The method of claim 1
   wherein the resist has been exposed;
   wherein the second resist has been exposed to a predetermined dose of radiation; and
   further comprising adjusting a lithography system to provide a different dose of radiation based on the comparison of the thermal signatures.

8. A method comprising:
   determining a thermal signature for a first sample, wherein determining the thermal signature for the first sample comprises determining a plurality of heat capacities at different temperatures, including a first heat capacity at a first temperature in the range of 50–100° C. and a second heat capacity at a second temperature in the range of 100–200° C., for the first sample of a first resist;
   determining a thermal signature for a second sample, wherein determining the thermal signature for the second sample comprises determining a plurality of heat capacities at the different temperatures, including a third heat capacity at the first temperature and a fourth heat capacity at the second temperature, for the second sample of a second resist; and
   comparing the thermal signature of the first sample to the thermal signature of the second sample, wherein comparing comprises comparing the first heat capacity to the third heat capacity and comparing the second heat capacity to the fourth heat capacity.

9. A method comprising:
   determining a thermal signature for a first sample, wherein determining the thermal signature for the first sample comprises determining a thermal signature for a first sample of an exposed radiation sensitive layer;
   determining a thermal signature for a second sample, wherein determining the thermal signature for the second sample comprises determining a thermal signature for a second sample of an exposed radiation sensitive layer;
   comparing the thermal signature of the first sample to the thermal signature of the second sample; and
   further comprising adjusting a lithography system to provide a different dose of radiation based on the comparison of the thermal signatures of the first and second samples.

10. The method of claim 9, wherein determining each of the thermal signatures comprises determining a maximum heat capacity.

11. The method of claim 9, wherein determining the thermal signatures comprises determining thermal signatures by a modulated differential scanning calorimetric analysis.

12. A method comprising: determining a thermal signature for a first sample of a first resist material that is known to be suitable for manufacturing integrated circuits in an integrated circuit manufacturing process by performing a calorimetric analysis of the first sample;

determining a thermal signature for a second sample of a second resist material that is not known to be suitable for manufacturing integrated circuits in the integrated circuit manufacturing process by performing a calorimetric analysis of the second sample;

comparing the thermal signature for the first sample to the thermal signature for the second sample; and inferring whether the second resist material is suitable for manufacturing integrated circuits in the integrated circuit manufacturing process based on the comparison of the thermal signatures.

13. The method of claim 12:

wherein the thermal signatures each comprise a plurality of heat capacities determined at different temperatures based on a modulated calorimetric analysis.

14. The method of claim 12, wherein each of the thermal signatures comprise a first heat capacity determined for a sample of unexposed resist, a second heat capacity determined for a sample of exposed resist, and a third heat capacity determined for a sample of previously calorimetrically analyzed resist.

15. A method comprising:

determining a thermal property for a sample of a multiple layer structure containing a first layer and a second layer by thermally analyzing the sample;

determining a thermal property for a sample of a third layer by thermally analyzing the sample, wherein the first and third layers have substantially the same composition; and using the thermal properties determined for the samples of the multiple layer structure and the third layer to determine a thermal property of the second layer of the multiple layer structure.

16. The method of claim 15:

wherein determining the thermal property for the sample of the multiple layer structure comprises determining a heat capacity by modulated differential scanning calorimetric analysis;

wherein determining the thermal property for the sample of the third layer comprises determining a heat capacity by modulated differential scanning calorimetric analysis; and wherein using comprises using the heat capacities for the samples of the multiple layer structure and the third layer to determine a heat capacity for the second layer.

17. The method of claim 16, wherein the first layer and the third layer comprise resists and the second layer comprises an anti-reflective layer.

18. The method of claim 16, wherein the first layer and the third layer comprise low dielectric constant layers and the second layer comprises an etch stop layer.

19. The method of claim 16, wherein the first layer and the third layer comprise low dielectric constant layers of substantially the same composition and the second layer comprises a low dielectric constant layer of a substantially different composition.

* * * * *